United States Patent [19]
Ragi et al.

[11] Patent Number: 5,811,625
[45] Date of Patent: *Sep. 22, 1998

[54] METHOD OF INDIRECT HEAT EXCHANGE FOR TWO PHASE FLOW DISTRIBUTION

[75] Inventors: Elias G. Ragi, Williamsville; Thomas J. Godry, Tonawanda, both of N.Y.

[73] Assignee: UOP LLC, Des Plaines, Ill.

[*] Notice: The term of this patent shall not extend beyond the expiration date of Pat. No. 5,625,112.

[21] Appl. No.: 566,623

[22] Filed: Dec. 4, 1995

Related U.S. Application Data

[63] Continuation-in-part of Ser. No. 174,510, Dec. 28, 1993, Pat. No. 5,531,266.

[51] Int. Cl.⁶ .............................. C07C 2/62; C07C 2/56
[52] U.S. Cl. ........................................... 585/709; 585/715
[58] Field of Search ...................................... 585/709, 715

[56] References Cited

U.S. PATENT DOCUMENTS

| | | | |
|---|---|---|---|
| 1,358,050 | 11/1920 | Audianne | 165/174 |
| 2,099,186 | 11/1937 | Anderegg | 165/174 X |
| 2,707,868 | 5/1955 | Goodman | 165/174 X |
| 4,572,287 | 2/1986 | Allo et al. | 165/115 X |
| 4,607,689 | 8/1986 | Mochida et al. | 165/174 |
| 4,769,511 | 9/1988 | O'Neill | 585/715 |
| 5,091,075 | 2/1992 | O'Neill et al. | 208/134 |
| 5,150,749 | 9/1992 | Bergmann et al. | 165/115 |
| 5,625,112 | 4/1997 | Ragi et al. | 585/709 |

FOREIGN PATENT DOCUMENTS

| | | | |
|---|---|---|---|
| 567362 | 2/1957 | Italy | 165/174 |
| 558510 | 1/1975 | Switzerland | 165/174 |
| 27198 | of 1898 | United Kingdom | 165/158 |
| 635793 | 4/1950 | United Kingdom | 165/174 |

*Primary Examiner*—Glenn Caldarola
*Assistant Examiner*—In Suk Bullock
*Attorney, Agent, or Firm*—Thomas K. McBride; John G. Tolomei

[57] ABSTRACT

The use of flow restrictors at the inlet of reactor cooling tubes significantly improves heat transfer and process performance in an acid catalyzed alkylation reaction process. Improved vaporization of the stream is achieved by equalizing the liquid distribution and the ratio of liquid and vapor entering each tube to overcome poor boiling film heat transfer. The invention relocates available pressure drop for equally subdividing the flow entering the heat exchanger into a plurality of heat exchanger inlet streams. Flow restrictors provide pressure drop at the inlets to each tube. This method and apparatus is particularly useful in contactors for the sulfuric acid catalyzed alkylation of olefinic and isoparaffinic hydrocarbons.

12 Claims, 2 Drawing Sheets

METHOD OF INDIRECT HEAT EXCHANGE FOR TWO PHASE FLOW DISTRIBUTION

CROSS REFERENCE TO RELATED APPLICATIONS

This application is a continuation-in-part of U.S. Ser. No. 08/174,510 filed Dec. 28, 1993, now U.S. Pat. No. 5,531,266.

FIELD OF THE INVENTION

This invention relates generally to the alkylation of hydrocarbons. More specifically, this invention relates to the indirect heat exchange of mixed phase fluids in the acid catalyzed alkylation of hydrocarbons.

BACKGROUND OF THE INVENTION

The use of enhanced boiling surfaces, and in particular nucleate boiling surfaces to increase the heat transfer film coefficient on boiling side heat transfer surfaces is well-known. U.S. Pat. No. 4,769,511 discloses the use of an enhanced nucleate boiling surface to improve the operation of a process for the alkylation of isoparaffins. The use of nucleate boiling surfaces to improve the operation of heat exchange equipment in the reforming of hydrocarbons is disclosed in U.S. Pat. No. 5,091,075.

The basic reaction of an acid catalyzed alkylation process is the conversion of isobutane and isobutene in the presence of a concentrated acid to produce iso-octane. The operation of this process with a concentrated sulfuric acid catalyst is well described in U.S. Pat. No. 4,769,511, the contents of which are herein incorporated by reference. In this process, olefins and isoparaffins are mixed on the shell side of a contactor that contains a plurality of tubes for indirect heat exchange. The product of the reaction is an emulsion of sulfuric acid and alkylate products that is decanted in an acid settler to separate a hydrocarbon stream containing the alkylate products from the acid. In a typical operation, the separated hydrocarbon stream undergoes a Joule-Thomson expansion that cools the liquid and generates a substantial amount of vapor. This two phase mixture of hydrocarbon liquid and vapor enters the inside of the heat exchange tubes in the contactor where further vaporization of the hydrocarbon stream removes heat generated by the alkylation reaction taking place on the shell side of the contactor.

Although enhanced boiling surfaces will usually improve the operation of exchangers and the processes in which the indirect heat exchangers operate, it was unexpectedly observed that enhanced boiling surfaces in an acid catalyzed alkylation process provided little or no benefit. The achievement of little or no benefit from the addition of an enhanced boiling surface was difficult to understand. Enhanced nucleate boiling surfaces greatly improve the heat transfer coefficient across the boiling film. An enhanced boiling surface having a porous boiling layer should provide about a ten fold increase in the nucleate boiling film coefficient. The contribution of the enhanced nucleate boiling surface in providing an improvement in overall heat transfer when used in flow boiling on the inside of a tube, of course, depends on the contribution to the heat transfer associated with nucleate boiling across the film and the contribution associated with convection. In some flow boiling applications, as much as 85% of the contribution to the overall heat transfer is attributable to convection. Nevertheless, in such cases even a 15 to 25% contribution of the nucleate boiling film heat transfer coefficient will allow the use of an enhanced boiling surface to demonstrate significant improvements in the overall heat transfer coefficient. Thus as long as their is some vapor generation, the addition of such a surface should provide a significant increase in the overall heat transfer performance.

It was surprisingly observed that heat transfer tubes coated with an enhanced porous boiling surface on their inside perform at essentially the same heat transfer rates as bare tubes. It was also unexpectedly encountered that tubes having an interior coating with an enhanced boiling surface demonstrated the same dependence on tube side flow rate as tubes with a bare interior wall. The failure to observe any increased performance from the addition of the enhanced boiling surface was difficult to understand.

Moreover, it was unexpectedly found that the bare tubes provided heat transfer rates much below those predicted by known heat transfer correlations. This lower than expected performance was in comparison with correlations that account for stratified flow. Thus, the cause of the observed low heat transfer performance was not readily understood.

It is an object of this invention is to improve the operation of acid contactors in alkylation processes that use boiling surfaces in multiple tube arrangements.

BRIEF DESCRIPTION OF THE INVENTION

This invention is a method for alkylating olefinic and paraffinic hydrocarbons that dissipates the heat of reaction by indirectly heating a mixed phase product stream through contact with a boiling surface located on the inside of a plurality of heat exchange tubes to vaporize a portion of the stream. The method at least partially relocates the location of a Joule-Thomson expansion from a throttling valve located upstream of a heater tube inlet chamber to the inlet of the heater tubes. This relocation of the expansion region to the inlet of each heat exchanger tube equalizes the distribution of liquid and the ratio of liquid and vapor entering each tube to overcome poor boiling film heat transfer. Relocation of the Joule-Thomson expansion eliminates variations in the amount of liquid and vapor entering each tube that was discovered to create stratified two phase flow in some of the tubes. The stratified two phase flow allows liquid to flow along one section of the tube interior and vapor to flow along another. The stratified layer of vapor renders the boiling surface that it contacts ineffective for boiling heat transfer. Only the areas covered by the liquid will have relatively high nucleate boiling heat transfer coefficients. Relocating the expansion to the cooling tube inlets equalizes the liquid distribution and the liquid and vapor ratios to the plurality of tubes without imposing additional pressure drop on the system. The uniform flow regime within the tubes replaces the undesirable stratified flow with highly desirable mixed phase annular flow. The mixed phase annular flow provides centralized mist surrounded by liquid on the outer portion of the tubes.

The method of this invention uses an inlet chamber that contains nozzles at the tube inlets to improve the uniformity of the total liquid distribution and the liquid to vapor ratio of the fluid that enters each tube in a plurality of heat exchange tubes. It is not necessary that the vaporization at the tube inlets of this alkylation process provide completely equal liquid distribution or liquid to vapor ratios to the inlet of each heat exchange tube. The benefits of this invention are achieved by avoiding extreme differences in the liquid distribution and the liquid to vapor ratio entering different heat exchange tubes. It has been found that distributing the liquid in a manner that improves the liquid distribution and evens out the liquid to vapor ratio of the fluid entering each heat exchange tube will provide significant benefits in the heat transfer coefficient provided by the boiling surface. Preferably, the division of the fluid entering the inlet chamber will result in the liquid to vapor ratio and the amount of liquid in the fluid at the inlet of each heat exchange tube varying by no more than 20% and more preferably by no more than 10%. Preferably the fluid streams enter the inlet chamber entirely in the liquid phase and all flashing occurs while the fluid passes through the tube inlets.

The flashing is typically provided by flow restrictors located at the inlets to the tubes. Locating flow restrictors just ahead of the inlet to the tubes can provide pressure drop that more evenly distributes the flow of fluid to the tubes and helps to maintain a uniform liquid to vapor ratio in all of the tubes. The flow restrictors utilize at least a portion of the pressure drop that was taken across the throttling valve upstream of the tubes. Therefore, this invention adds no additional pressure drop requirements to the system, but shifts a portion of the pressure drop that is already provided.

In one embodiment, this invention is a process for alkylating isoparaffinic hydrocarbons with olefinic hydrocarbons in the presence of an acid catalyst. The process includes steps of reacting the isoparaffinic hydrocarbons and olefinic hydrocarbons in the presence of acid catalyst to form alkylate, separating a hydrocarbon mixture into an acid phase and a hydrocarbon phase, reducing the pressure on the hydrocarbon phase to refrigerate and vaporize volatile hydrocarbons and passing the refrigerated hydrocarbon phase into contact with a boiling surface located on the interior of a plurality of heat exchange tubes. Vaporization of the hydrocarbons in contact with the enhanced boiling surface effects indirect heat exchange to cool the reaction mixture which is in contact with the exterior of the heat exchange tubes. This invention improves the alkylation process by passing the hydrocarbon phase to a tube inlet chamber that supplies the hydrocarbon phase to a plurality of heat exchange tube inlets and vaporizes a portion of liquid phase hydrocarbons at the inlet of each heat exchange tube. When a mixed phase hydrocarbon stream enters the inlet chamber, a distributor may also divide each of the inlet streams in a manner that equalizes the distribution of liquid to vapor to the inlet of each heat exchange tube.

Additional objects, embodiments, and details of this invention are set forth in the following detailed description of the invention.

DETAILED DESCRIPTION OF THE INVENTION

Figure 1:
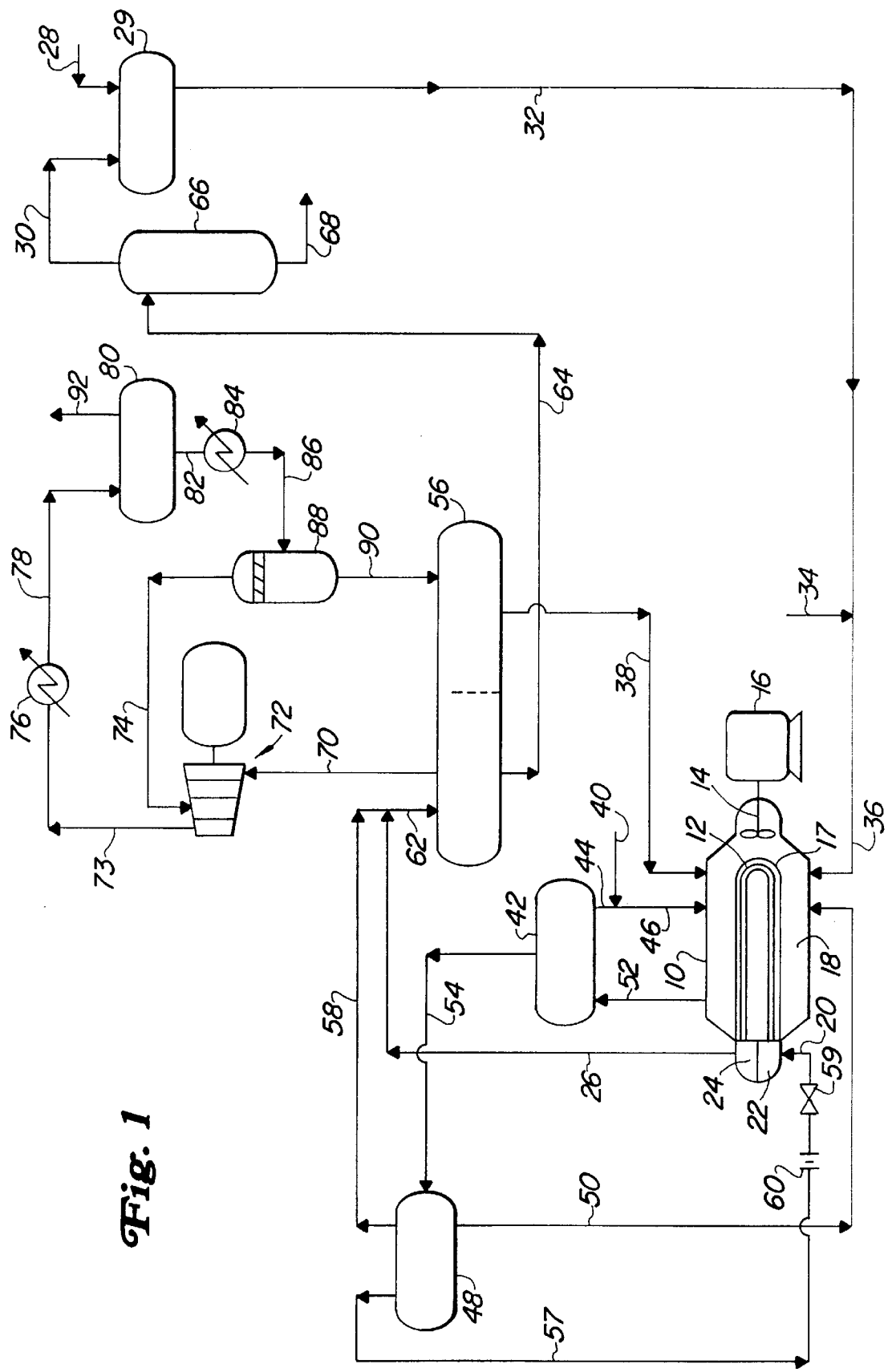
FIG. 1 is a simplified flow diagram of an alkylation process.

The method of this invention is broadly applicable to any alkylation process arrangement that partially or fully vaporizes a mixed phase hydrocarbon stream on the interior of a plurality of heat exchanger tubes by contact with a boiling surface to indirectly cool the outer surface of the heat exchange tubes. In order to achieve the benefits of this invention, the fluid passing through the interior of the heat exchange tubes must have a mixed phase. The invention is most useful when the fluid has a high concentration of vapor in the tubes. Preferred concentrations for vapor entering the inlet chamber of the alkylation reactor are in the range of from 0 to 30 wt %. Such weight percentages of vapor to liquid will typically result in 0 to 99% by volume of vapor.

This invention benefits fluids passing through the heat exchange tubes at both high and low flow rates. In most alkylation process applications, the flow rate for a tube having a typical outside diameter of from ¾ to 1 inch would fall in a range of from 100 to 400 pounds per hour per tube. This invention will provide improved boiling film heat transfer coefficients at both the high and low end of such a range. It is preferred that the flow rate through tubes having the typical outside diameter is greater than about 150 lbs/hr/tube to avoid a stratified flow regime.

The enhanced boiling surface which may be used on the inside of the heat exchange tubes can consist of any known surface that will provide the desired boiling enhancement over ordinary bare tube walls. Such enhanced boiling surface heat exchange tubes are discussed in, for example, U.S. Pat. Nos. 3,384,154, 3,821,018, 4,064,914, 4,060,125, 3,906,604, 4,216,826 and 3,454,081 all of which are incorporated herein by reference. These enhanced tubes are made in a variety of different ways which are well known to those skilled in the art. For example, such tubes may comprise annular or spiral cavities extending along the tube surface made by mechanical working of the tube. Alternatively, fins may be provided on the surface. So too, the tubes may be scored to provide ribs, grooves, a porous layer and the like.

Generally, the more efficient enhanced tubes are those having a porous layer on the boiling side of the tube which can be provided in a number of different ways well known to those skilled in the art. In one such method, as described in U.S. Pat. No. 4,064,914, the porous boiling layer is bonded to one side of a thermally conductive wall. The porous boiling layer is made of thermally conductive particles bonded together to form interconnected pores.

An essential characteristic of the porous surface layer is the interconnected pores of capillary size, some of which communicate with the outer surface. Liquid to be boiled enters the subsurface cavities through the outer pores and from the subsurface cavities enters interconnecting pores. The liquid is heated by the metal forming the walls of the cavities. At least part of the liquid is vaporized within the cavity and resulting bubbles grow against the cavity walls. Vapor bubbles eventually emerge from the cavity through the outer pores and then rises through the liquid film over the porous layer for disengagement into the gas space over the liquid film. Additional liquid flows into the cavity from the interconnecting pores and the mechanism is continuously repeated.

The use of concentrated liquid acids as catalysts for the alkylation of olefinic and paraffinic hydrocarbons is well known. Hydrofluoric and sulfuric acids are most widely used in these processes. This invention is especially suited is the acid alkylation of olefins and paraffins to produce iso-octane. The preferred form of the alkylation process uses a sulfuric acid catalyst in a process that auto-refrigerates a hydrocarbon phase to provide cooling in the reactor.

A specific arrangement of a process for the alkylation of $C_4$ olefins and paraffins is shown in FIG. 1. Referring to FIG. 1, an acid contactor in the form of a reactor shell 10 is equipped with a "U-shaped" heat exchange tube bundle 12. Tube bundle 12 consists of "U-shaped" heat exchange tubes having enhanced boiling surfaces provided on the inside. A propeller or pump impeller 14 is driven to circulate fluid on the shell side of the tube bundle 12. A motor 16 drives the propeller which circulates fluid into the center of a circulation tube 17 and through an annular space 18. Tube side fluid enters the contactor via line 20 and passes through an inlet chamber 22 which distributes the fluid to the tube bundle 12. An outlet chamber 24 collects the tube side fluid which exits the contactor through a line 26.

Isoparaffins enter the process from a line 28 and are combined with recycled hydrocarbons from a line 30 in a drum 29. Line 32 carries the combined isoparaffinic feed into combination with an olefin feed entering the process via a line 34. The combined feedstream enters the contactor via line 36. The contactor also receives a flash recycle stream of hydrocarbons via a line 38 from a drum 56. Make-up acid for the process enters via a line 40 and is combined with recycle acid from an acid settler 42 that passes through a line 44. The combined acid stream enters contactor 10 via line 46. An additional flow of acid passes from an effluent settler 48 via a line 50 and into contactor 10.

An emulsion containing acid and alkylate product passes out of contactor 10 via a line 52 and into acid settler 42. A line 54 carries the emulsion over to the effluent settler 48. Alkylate product flows from the effluent settler and through the contactor via lines 57, 20 and 26 as previously described. In conventional cases the alkylate product which passes overhead from the settler 48 is expanded by passing through a control valve 59 before supplying the fluid through line 20. In the operation of this invention, control valve 59 acts as a throttling valve that provides only a portion of the pressure drop for expansion of the hydrocarbon stream. A restriction orifice 60 provides means for measuring the flow from line 57. Effluent from line 26 empties via line 62 into a trap defined by a partitioned portion of flash drum 56. A portion of the settler overhead effluent by-passes contactor 10 via line 58 and passes directly to the trap of the partitioned portion of drum 56 via line 62.

Vapor and liquid portions from line 62 are separated in the suction trap of drum 56. Line 64 carries liquid alkylate products over to a deisobutanizer 66 that separates alkylate products into a product stream 68 and returns feed isoparaffins, via a line 30, to drum 29 for recycle to the contactor.

Separated vapors and flash vapors from an economizer 88 of the compression section combine in the flash portion of suction drum 56 for withdrawal by line 70. Vapor from line 70 enters the suction side of a compressor 72 which raises the pressure of the vapor from line 70. An intermediate stage of compressor 72 receives an economizer vapor stream carried by line 74. The compressor pushes compressed vapors into a line 73 and through a condenser 76. Line 78 passes cooled vapors to an accumulator 80. Liquid from the accumulator, taken by line 82 and cooled by a condenser 84, passes via line 86 into economizer 88 that separates vapor for recycle to the intermediate stage of the compressor via line 74 and supplies the condensed hydrocarbon containing liquid carried by line 90 to drum 56. Vapors from accumulator 80 pass overhead via a line 92 and, typically, into a depropanizer.

In a typical acid catalyzed alkylation process the reactor effluent stream containing the alkylate product (shown as 57 in FIG. 1) is throttled from a pressure of about 60 to 70 psi to a pressure of about 5 to 50 psi. As a result of this Joule-Thomson expansion, the hydrocarbon liquid is normally cooled to between 30° to 40° F. and vapor is generated. Typically, this vapor will be in a range of between 3 to 10% by weight and 90 to 98% by volume. The two phase mixture of hydrocarbon liquid and vapor enters the tubes in the contactor which removes the heat generated by the alkylation reaction taking place on the shell side of the contactor.

Figure 2:
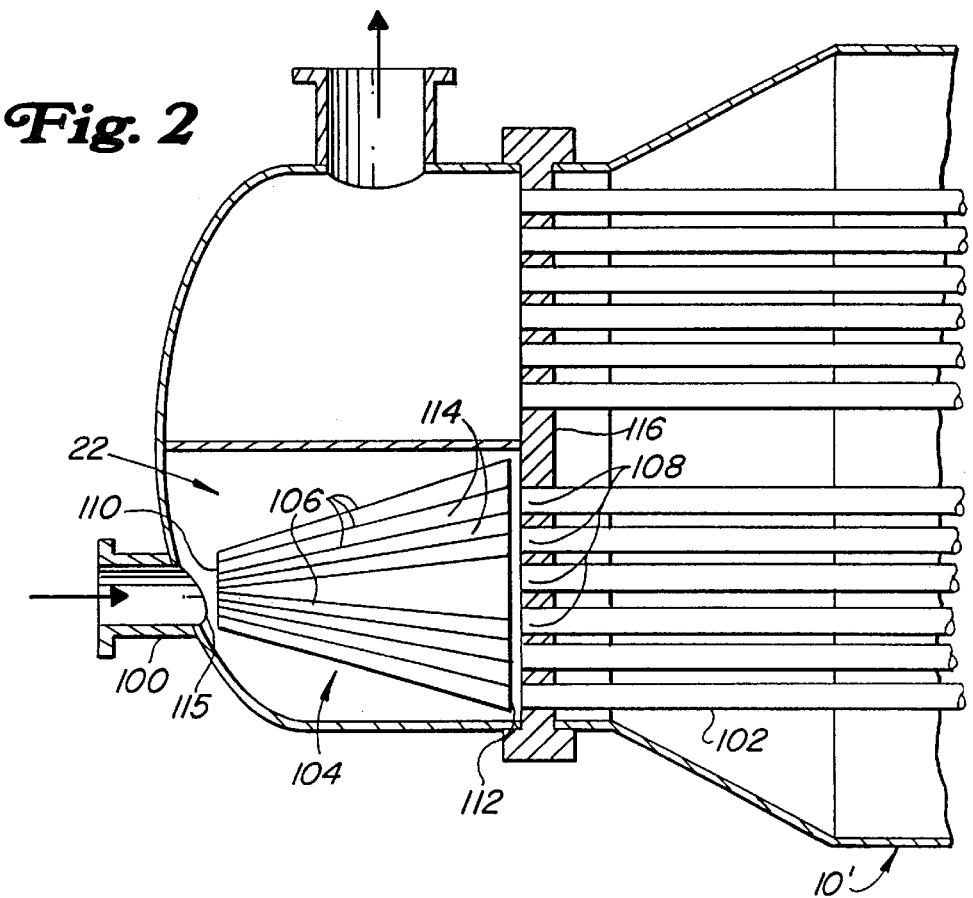
FIG. 2 is a schematic illustration of an exchanger incorporating a flow distributor of this invention.
Figure 3:
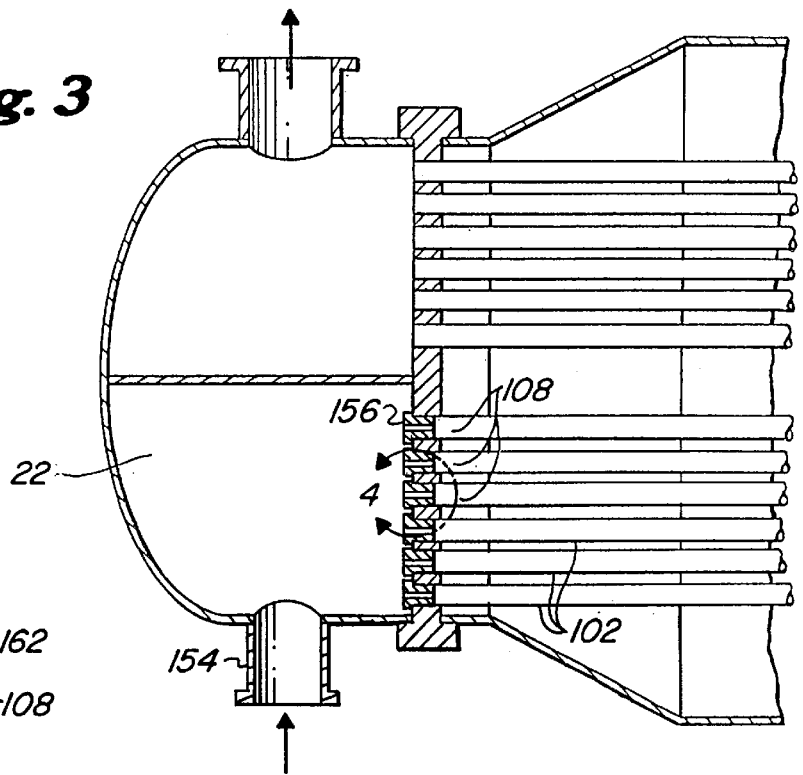
FIG. 3 shows the location of a plurality of plugs in the inlet chamber for distributing flow.

This invention uses at least a portion of the pressure reduction for the vaporization of the hydrocarbon phase to equalize the liquid distribution and the ratio of liquid to vapor entering the inlets of the tubes. FIG. 3 shows such an arrangement wherein the fluid from line 20 enters the inlet chamber 22 in liquid phase through a nozzle 154. In conjunction with the arrangement shown in FIG. 2, the Joule-Thomson expansion is preferably not performed prior to fluid entering inlet chamber 22 as previously described so that all of the fluid can enter the inlet chamber in a subcooled liquid phase. The inlet chamber has located within it a series of perforated plugs 156 located ahead of inlets 108 of tubes 102. The plugs 156 can be located in the inlet chamber 22 or extend into the tubes in which case the inlet chamber is considered to include the portion of the tube containing the plug and the inlet of the tube located after the outlet of the plug.

It is not necessary that all of the pressure drop associated with the Joule-Thomson expansion be taken across the plugs 156. A substantial portion of the pressure drop may still be effected over an expansion device such as control valve 59. The advantages of liquid phase distribution may be obtained by only taking the final portion of the pressure drop across plugs 156. This final portion is that pressure drop over which there is a transition from a subcooled liquid to a two phase mixture. Typically the pressure drop associated with the transition is from about 5 to 15 psi.

Figure 4:
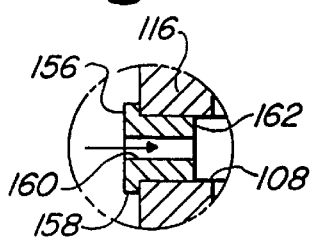
FIG. 4 shows a detail of a plug and the orifice opening defined thereby.

FIG. 4 shows the plug arrangement in more detail. The plug 156 is located just ahead of the inlet portion 108 of the tube. Plug 156 has a shoulder 158 that abuts a tube sheet 116. As liquid passes through restricted opening 160 and exits out of end 162 of the plug, the pressure drop induced by plug 156 causes the Joule-Thomson expansion of the liquid to occur just at the outlet of the plug. Therefore, the inlet chamber divides the liquid fluid evenly due to the pressure drop associated with each plug and each plug which comprises a portion of the inlet chamber forms separate streams having equal ratios of liquid to vapor in each of the tubes just as the fluid exits the inlet chamber.

When a mixed phase enters the inlet of the alkylation reactor, the invention further benefits from the use of a distributor in the inlet chamber of the contactor. Inlet chamber 22 can contain a number of different distribution devices that will distribute the alkylate product entering the inlet of tube bundle 12. FIG. 2 schematically shows the inlet and outlet portion for the tube side of a contactor 10' which is similar to the contactor 10. As compared to FIG. 1, FIG. 2 shows contactor 10' with a modified nozzle 100 having a center line parallel to the center line of heat exchange tubes 102. One method of dividing the flow through the inlet chamber in a manner to equalize the distribution of liquid and the ratio of liquid to vapor entering each tube is by using a two phase distributor as shown schematically in FIG. 2 by number 104. The distributor depicted in FIG. 2 consist of a series of concentric vanes 106. Vanes 106 define flow channels 114. The vanes are arranged to divide the flow entering nozzle 100 into a plurality of inlet streams that pass through flow channels 114 and are directed into the restricted openings of inlets 108 of the tubes 102. The vanes collectively define the cross sectional area of each of the flow channels at the inlet end 110 and the outlet end 112. The cross-sectional areas of the flow channels 114 at the inlet end 110 and the outlet end 112 are proportional to the number of tube inlets 108 into which each individual channel 114 directs its portion of the inlet stream. The inlet end 110 of the distributor 104 is located close to the outlet end 115 of nozzle 100. Similarly, the outlet of distributor 112 is located close to the tube inlets 108. The outer perimeter of distributor 104 at the outlet 112 will preferably match the outer periphery of tubes 102. Preferably, outlet end 112 is less than 1 inch from the tube sheet 116 containing the inlets 108 for tubes 102. The inlet end of distributor 110 will also have an outer periphery that closely matches the outer diameter of nozzle 100. Inlet end 110 for distributor 104 will also preferably have a location within 1 inch or less of the outlet end 115 of nozzle 100. It is also possible to extend inlet end 110 directly into nozzle 100 to insure a complete division of the fluid stream entering nozzle 100 into a plurality of inlet streams. The distributor 104 may be added during the initial fabrication of the contactor or retrofitted into an existing contactor.

EXAMPLES

The operation of reactor/contactors in an acid catalyzed reaction zone for the alkylation of hydrocarbons were measured, calculated and evaluated to determine the benefits provided by applying a distribution device. For a conventional bare tube reactor/contactor, the internal circulation rate of the hydrocarbon and acid emulsion on the shell side of the contactor is in a range of about 40,000 to 60,000 gallons per minute. The overall heat transfer coefficient of the contactor is from 35 to 55 BTU/HR-FT$^2$-°F. depending on the flow rate, and capacity. The corresponding emulsion heat transfer coefficient i.e., shell side heat transfer coefficient, of prior art reactor/contactors is about 90 to 150 BTU/HR-FT$^2$-°F.

Example 1

In order to show the surprising effect of distributing fluid in a manner to equalize liquid and vapor to the tubes within a reactor/contactor for the acid catalyzed alkylation of hydrocarbons, a series of field measurements were obtained and compared with known heat transfer correlations. Field measurements were taken from an acid catalyzed alkylation process using a contactor that operated at an internal circulation rate of 40,000 GPM on the emulsion side, i.e. shell side of the contactor, and at a viscosity of about 43 CP. Measurements determine that the average heat transfer coefficient across the tubes of the contactor was 48 BTU/HR-FT$^2$-°F. The corresponding shell side film heat transfer coefficient was determined using an experimental correlation to equal 136 BTU/HR-FT$^2$-°F.

Example 2

By dividing the fluid stream entering the contactor and equalizing the total liquid and the ratio of vapor and liquid in the fluid entering each of the tubes, the bare tube heat transfer coefficient can be improved. Based on calculation using known heat transfer correlations, the tube side boiling heat transfer coefficient for the bare tubes with a well distributed fluid was determined to be 325 BTU/HR-FT$^2$-°F. Overall heat transfer coefficients for the bare tubes can be increased to 70 BTU/HR-FT$^2$-°F. respectively. Therefore distribution means will improve the bare tube operation.

Example 3

Based on a tube side coefficient calculated from laboratory data and known heat transfer correlations, the calculated boiling coefficient on the tube side with enhanced nucleate boiling surface tubes was determined. With a well distributed fluid the tubes with the enhanced nucleate boiling surface will have a tube side heat transfer coefficient of 800 BTU/HR-FT$^2$-°F. By dividing the fluid stream entering the contactor and to evenly distribute liquid and equalizing the ratio of vapor and liquid in the fluid entering each of the tubes, the enhanced tube heat transfer coefficient will be greatly improved. The overall coefficient for the enhanced nucleate boiling surface tubes will increase to 84 BTU/HR-FT$^2$-°F. Therefore, although distribution means will improve the bare tube operation, more surprisingly the enhanced boiling surface has much more sensitivity to the control of liquid distribution and vapor to liquid ratios so that the application of distribution means provides an unexpectedly greater benefit.

The bare tube and the enhanced nucleate boiling surfaces both benefit from the distribution method of this invention. As the examples show, the bare tube and enhanced boiling surface tube performance are improved by factors of 1.46 and 1.75 respectively.

We claim:

1. In a process of alkylating isoparaffinic hydrocarbons with olefinic hydrocarbon comprising the steps of reacting isoparaffinic hydrocarbons and olefinic hydrocarbons in the presence of acid catalyst in a reaction zone to form alkylate, withdrawing a mixture of hydrocarbons with acid catalyst as effluent from said reaction zone, separating said effluent into an acid phase and a hydrocarbon phase in a first separating zone, reducing the pressure on the hydrocarbon phase to refrigerate it and vaporize volatile hydrocarbons, passing the refrigerated hydrocarbon phase into contact with a boiling surface located on the interior of a plurality of heat exchange tubes to effect indirect heat exchange with the reaction mixture of hydrocarbons and catalyst in the reaction zone and to remove exothermic heat of reaction and vaporize further volatile hydrocarbons in the hydrocarbon phase, separating the liquified portion of the hydrocarbon phase from the vapor portion thereof in a second separating zone, fractionating the liquid portion of the hydrocarbon phase to remove alkylate, recovering isoparaffinic hydrocarbons from said vapor phase and recycling isoparaffinic hydrocarbon hydrocarbons as a reactant in the reaction zone, the improvement which comprises:

passing the hydrocarbon phase to a tube inlet chamber that supplies said hydrocarbon phase to said plurality of heat exchange tubes to divide the hydrocarbon phase into a plurality of tube inlet streams that each enter the interior of one of said heat exchange tubes and reducing the pressure of said tube inlet streams at the inlet of each tube to vaporize liquid hydrocarbons and supply at least a portion of said refrigeration.

2. The improvement of claim 1 wherein the vapor to liquid ratio and the amount of liquid of each of each tube inlet streams varies by no more than 20%.

3. The improvement of claim 1 wherein said hydrocarbon phase is divided into a plurality of chamber inlet streams in said tube inlet chamber and said chamber inlet stream supply said hydrocarbon phase for said tube inlet streams.

4. The improvement of claim 1 wherein the boiling surface is an enhanced boiling surface comprising a porous boiling layer.

5. The improvement of claim 1 wherein said hydrocarbon phase enters said chamber as liquid.

6. The improvement of claim 1 wherein said hydrocarbon phase passes through said tubes at a mass rate of 100 to 400 lb/hr and said tubes have an outside diameter of from ¾ to 1 inch.

7. The improvement of claim 1 wherein each of said tube inlet streams passes through a restriction orifice to reduce the pressure at the inlet of each tube.

8. The improvement of claim 1 wherein the pressure drop at the inlet of each tube is at least 5 psig.

9. The improvement of claim 1 wherein said hydrocarbon phase passes through a flow restriction before entering said inlet chamber.

10. The improvement of claim 1 wherein said second fluid is passed into said chamber under mixed phase conditions.

11. The improvement of claim 3 wherein each of said chamber inlet streams directs fluid into the inlet of more than one of said heat exchange tubes.

12. The improvement of claim 3 wherein each of said heat exchange tubes receives fluid from more than one of said inlet streams.

* * * * *